(12) United States Patent
Stogniew et al.

(10) Patent No.: US 6,586,476 B1
(45) Date of Patent: Jul. 1, 2003

(54) METHODS FOR THE TREATMENT OF NEPHRO-DISORDERS USING AMINOTHIOL COMPOUNDS

(75) Inventors: Martin Stogniew, Blue Bell, PA (US); David S. Alberts, Tucson, AZ (US); Edward H. Kaplan, Skokie, IL (US)

(73) Assignee: MedImmune Oncology, Inc., Gaithersburg, MD (US)

( * ) Notice: Subject to any disclaimer, the term of this patent is extended or adjusted under 35 U.S.C. 154(b) by 0 days.

(21) Appl. No.: 09/429,290

(22) Filed: Oct. 28, 1999

Related U.S. Application Data

(62) Division of application No. 08/987,550, filed on Dec. 9, 1997, now Pat. No. 5,994,409.

(51) Int. Cl.$^7$ ............... A61K 31/66; A61K 31/13; A61K 31/16; A61K 31/095
(52) U.S. Cl. ............... 514/665; 514/114; 514/649; 514/608; 514/706
(58) Field of Search ............... 514/114, 665, 514/649, 608, 706

(56) References Cited

U.S. PATENT DOCUMENTS

| | | | | |
|---|---|---|---|---|
| 4,656,034 A | | 4/1987 | Sarnoff | 424/94 |
| 4,735,210 A | | 4/1988 | Goldenberg | 128/654 |
| 4,742,050 A | | 5/1988 | Yuhas et al. | 514/34 |
| 5,091,180 A | | 2/1992 | Walker et al. | 424/944 |
| 5,112,954 A | | 5/1992 | Abrams et al. | 530/391.9 |
| 5,167,947 A | | 12/1992 | Geary | 424/11 |
| 5,217,964 A | | 6/1993 | Edwards et al. | 514/104 |
| 5,434,145 A | | 7/1995 | Edwards et al. | 514/108 |
| 5,554,655 A | * | 9/1996 | Thoene | 514/665 |
| 5,605,931 A | | 2/1997 | Hanson | 514/530 |
| 5,618,823 A | | 4/1997 | Cavelletti et al. | 514/283 |
| 5,776,095 A | | 7/1998 | Goldenberg | 604/20 |
| 5,804,571 A | * | 9/1998 | Schein | 514/114 |
| 5,866,591 A | | 2/1999 | Gatlin et al. | 514/329 |
| 5,919,934 A | | 7/1999 | John et al. | 546/247 |
| 5,972,986 A | | 10/1999 | Seibert et al. | 514/406 |
| 6,028,114 A | | 2/2000 | Quash | 514/665 |
| 6,054,622 A | | 4/2000 | Zhang et al. | 568/62 |
| 6,066,688 A | | 5/2000 | Hausheer | 514/492 |
| 6,075,053 A | | 6/2000 | Hausheer | 514/578 |
| 6,096,399 A | | 8/2000 | Ayer et al. | 424/473 |
| 6,106,866 A | | 8/2000 | Ranny | 424/499 |
| 6,110,891 A | | 8/2000 | Pusztai et al. | 514/8 |
| 6,114,394 A | | 9/2000 | Edwards et al. | 514/646 |

FOREIGN PATENT DOCUMENTS

| | | |
|---|---|---|
| WO | WO 88/07942 | 9/1989 |
| WO | WO 99/30705 | 6/1999 |

OTHER PUBLICATIONS

Hirschel–Scholz et al. 109CA:48093, 1988.*
Polla et al, 113CA:227230, 1990.*
Pedrotti et al, 117CA:440123, 1992.*
Capizzi, 126CA:28347, 1996.*
R.L. Capizzi, 1996, "The Preclinical Basis for Broad–spectrum Selective Cytoprotection of Normal Tissues from Cytotoxic Therapies by Amifostine (Ethyol©)," *European Journal of Cancer,* 32A(4):S5–S16.
NIH Publication No. 89–2141, Revised November 1988.
Petrotti et al., 1992, "Protection from hypoxemia–induced renal dysfunction by the thiophosphate WR–2721," *Kidney International,* 41:80–87.
Polla et al., 1990, "Protection From Cellular Oxidative Injury and Calcium Intrusion by N–(2–Mercaptoethyl)–1, 3–Propanediamine, WR 1065," *Biochemical Pharmacology,* 40(7):1469–1475.
Hirschel–Scholz et al., 1988, "Protection from progressive renal failure and hyperparathyroid bone remodeling by WR–2721," *Kidney International,* 33:934–941.
Zadeii et al., 1991, "Stability of Ethiofos (NSC–29691) In Aqueous Solution and Solid Phase Formulation" (PDD 7184), *Pharm. Res.* 8(10):S–172.
"Drug Information For The Health Care Provider," 1987, *United States Pharmacopeia Dispensing Information, 7$^{th}$ Edition,* (1):1217–19.
Phillips et al., 1982, "Differential Protection Against Alkylating Agent Injury In Tumors And Normal Tissues," *Radioprotectors and Anticarcinogens,* 735–48.
Valeriote et al, 1982, "Protection and Potentiation of Nitrogen Mustard Cytoxicity by WR–2721," *Cancer Research,* 42:4330–31.
Valeriote et al, 1984, "Dose and Interval Relationship For The Interaction Of WR–2721 And Nitrogen Mustard With Normal and Malignant Cells," *International Journal of Radiation, Oncology, Biol. Phys.,* 10:1561–1564.
Yuhas et al., 1980, "Treatment of Tumours With The Combination of WR–2721 and Cis–dichloro–diammineplatinum (II) or Cyclophosphamide,") *British Journal of Cancer,* 42:574–585.
Davidson et al, "Biological characteristics of some improved radioprotectors," *Radiation Sensitizers,* 1980 pp. 309–320.

* cited by examiner

*Primary Examiner*—Russell Travers
(74) *Attorney, Agent, or Firm*—Pennie & Edmonds, LLP

(57) ABSTRACT

The present invention relates to new uses of S-2-(3-aminopropylamino)ethyl dihydrogen phosphorothioate, (amifostine) and other aminothiol compounds to treat and reverse toxicities caused by therapeutic agents, radiation treatment or diabetes. In particular, the invention provides a method for treating neurotoxicity and nephrotoxicity associated with the administration of chemotherapeutic agents.

19 Claims, 1 Drawing Sheet

METHODS FOR THE TREATMENT OF NEPHRO-DISORDERS USING AMINOTHIOL COMPOUNDS

Figure 1:
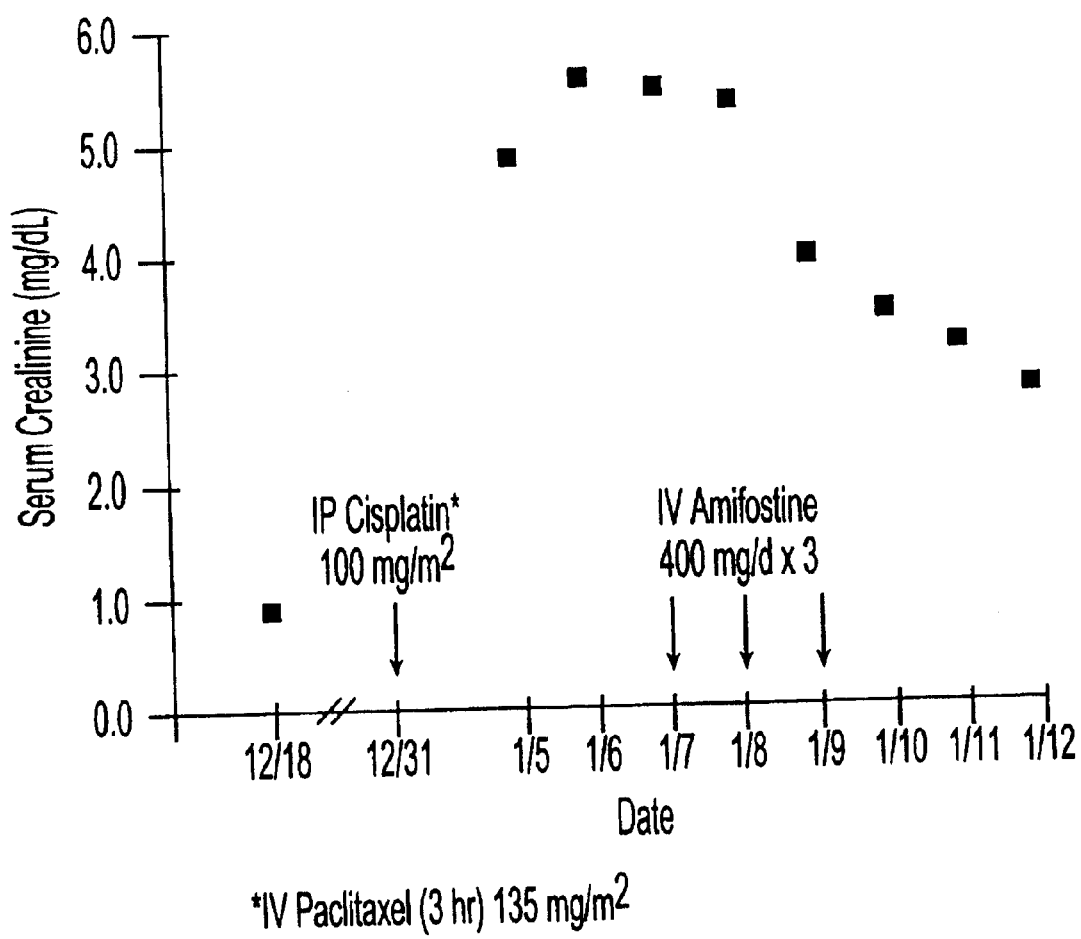

This is a division of application Ser. No. 08/987,550 filed Dec. 9, 1997 now U.S. Pat. No. 5,994,409, now allowed which is incorporated by reference herein in its entirety.

1. FIELD OF THE INVENTION

The present invention relates to new uses for S-2-(3-aminopropylamino)ethyl dihydrogen phosphorothioate, also known as amifostine, its salts, hydrates, esters, metabolites, functional derivatives, functional analogues, and related aminothiol compounds, to treat and reverse certain toxicities, including toxicities caused by drugs and/or radiation therapy, and to treat certain disorders, particularly neuro- and nephro-disorders.

2. BACKGROUND OF THE INVENTION

2.1. Aminothiol Compounds

The compound S-2-(3-aminopropylamino)ethyl dihydrogen phosphorothioate (which is also known as amifostine, ethiofos, Ethyol®, NSC 296961, and WR-2721 and which will hereinafter be referred to as "amifostine") and other aminothiol compounds are disclosed in U.S. Pat. No. 3,892,824 to Piper et al. These compounds were originally developed as antiradiation agents (radio-protectants), in particular to be used prior to exposure to x-ray or nuclear radiation, to protect against the harmful effects of such exposure which may be encountered during military conflicts.

In addition to its utility as a military antiradiation agent, amifostine has demonstrated excellent utility as a non-military radioprotectant and chemoprotectant, i.e., as a protectant administered prior to therapy to reduce the undesirable adverse effects which arise during the use of chemotherapy and radiation therapy in the treatment of cancer. Nygaard et al., eds., 1983, *Radioprotectors and Anticarcinogens*, Academic Press, Inc., New York, pp. 73–85; Grdina et al., 1985, "Radioprotector WR-1065 Reduces Radiation-Induced Mutations of the HGPRT Locus in V79 Cells," *Carcinogenesis* (London) 6:929–931. In addition, these compounds have been reported to afford protection against the adverse effects of chemotherapeutic agents, for example, alkylating agents such as cisplatin and carboplatin, when administered before or concurrently with the chemotherapeutic agent. Jordan et al., 1982, "Modulation of cis-platinum renal toxicity by the Radioprotective agent WR-2721", *Exp. Mol. Pathol.* 36:297; Doz et al., 1991, "Experimental Basis for Increasing the Therapeutic Index of Carboplatin in Brain Tumor Therapy by Pretreatment With WR-Compounds", *Cancer Chemother. Pharmacol.* 28:308. Similarly, it has been reported that amifostine has been used experimentally prior to therapy to protect HIV-infected patients (AIDS) from the harmful side effects of 3'-azido-3'-deoxythymidine (AZT) therapy. International Published Application WO 90/14007, published Nov. 29, 1990. Amifostine and its derivatives have been shown to exert these reported protective effects without affecting the beneficial properties of the administered therapeutic agents. This is, in the case of chemotherapy, believed to be due to the selective uptake of the protective thiol and other metabolites into normal tissue. Yuhas, 1980, "Active versus Passive Absorption Kinetics as the basis for Selective Protection of Normal Tissues by WR-2721", *Cancer Res.* 40:1519-1524; Yuhas, 1979, "Differential Protection of Normal and Malignant Tissues Against the Cytotoxic Effects of Mechlorethamine" *Cancer Treat. Rep.* 63:971–976.

Amifostine and related aminothiol compounds have also been shown to stimulate bone marrow growth. See U.S. patent application Ser. No. 08/390,713; International Published Application WO 96/25045 published Aug. 22, 1996; List et al., "Amifostine Stimulated Formation of Multipotent Progenitor and Generated Macroscopic Colonies in Normal and Myelodysplastic Bone Marrow," *Proc. Am. Soc. Clin. Oncol.* 15:449 [1403] [Abstract]. Currently, amifostine is in Phase II clinical trials as a bone marrow stimulant in patients suffering from myelodysplastic syndrome. List et al., 1996, "Amifostine Promotes Multilineage Hematopoiesis in Patients with Myelodysplastic.Syndrome (MDS): Results of a Phase I/II Clinical Trial,"*Am. J. Hem.* 1 (Abstract); List et al., 1996, "Amifostine Promotes in vitro and in vivo Hematopoiesis in Myelodysplastic Syndromes," *Chem. Found Sympos.* (Abstract); List et al., 1996, "Amifostine Promotes Multilineage Hematopoiesis in Patients with Myelodysplastic Syndrome (MDS): Results of a Phase I/II Clinical Trial," Abstract, 8th Annual Meeting, American Society of Hematology, Orlando, Fla. Pre-exposure with aminothiol compounds is capable of causing the bone marrow function to more rapidly recover following chemotherapy. List et al., 1996, "Amifostine Protects Primitive Hematopoietic Progenitors Against Chemotherapy Cytotoxicity," *Semin. Oncol.* 23 (4) Supp. 8:58–63.

Presently, amifostine is indicated to reduce the cumulative renal toxicity associated with repeated administration of cisplatin in patients with advanced ovarian or non-small cell lung cancer. *Physicians' Desk Reference*, 51st ed. 1997, p. 485–486. The recommended starting dosage for adults in an FDA-approved indication is 910 mg/m$^2$ administered once daily as a 15-minute intravenous (i.v.) infusion, starting 30 minutes prior to chemotherapy. However, clinical trials have used doses as low as 100 mg.

U.S. Pat. Nos. 5,567,686 and 5,488,042, both to Grdina, allege that the administration of an aminothiol compound before irradiation of a mammal affords protection against genotoxic mutagenesis. Although the U.S. Pat. No. 5,488,042 patent discloses administering an aminothiol up to about three hours after irradiation, both patents focus solely on prevention of mutations, rather than the treatment or reversal of radiation- or chemotherapy-induced damage. Further, the Grdina patents are silent as to the use of any aminothiol compound in humans to treat chemotherapy- or radiation-induced disorders and toxicities including neuro-, nephro-, hematological or mucosal disorders.

Nagy et al., 1986, "Protection Against cis-Diamminedichloroplatinum Cytotoxicity and Mutagenicity in V79 Cells by 2-[(Aminopropyl)amino]ethanthiol," *Cancer Research* 46:1132–1135, disclose that the free thiol metabolite of amifostine, also known as WR-1065, protects against cytotoxicity in V79-B310H Chinese hamster cells when administered before, during and immediately after treatment of the cells with cis-diamminedichloroplatinum (cis-DDP, "cisplatin"). Although some protection against cell death was observed under all conditions, Nagy et al. report that maximum protection was obtained when WR-1065 was present in the cell growth medium for 30 minutes prior to exposure of cells to cisplatin. In addition, Nagy et al. state that little if any difference in the magnitude of protection against cell killing was seen whether the WR-1065 was present either during or immediately following cisplatin exposure.

Treskes et al., 1992, "Effects of the Modulating Agent WR-2721 and its Main Metabolites on the Formation and Stability of Cisplatin-DNA Adducts in Vitro in Comparison to the Effects of Thiosulphate and Diethyldithiocarbonate," *Biochemical Pharmacology* 43(5):1013–1019 investigated the ability of amifostine and its main metabolites, WR-1065 and WR-33278, to prevent formation of adducts of cisplatin with the DNA of salmon sperm. They found that amifostine, WR-1065 and WR-33278 caused a decrease in the platination of salmon sperm in vitro when the compounds were present concomitantly with cisplatin. It was also observed that part of the already formed cisplatin-DNA adducts is disrupted during post-incubation with subject compounds, but this decrease in adduct levels was small compared to those obtained during co-incubations. Treskes et al. speculated that conformational changes in DNA induced by the WR-1065 metabolite of amifostine observed by other researchers might provide a rational for applying amifostine after cisplatin administration.

However, Treskes et al. later reported in 1993, "WR2721 as a Modulator of Cisplatin- and Carboplatin-induced Side Effects in Comparison with Other Chemoprotective Agents: A Molecular Approach," *Cancer Chemother. Pharmacol.* 33:93–106, that neither WR-1065 nor WR-2721 (amifostine) could protect cells from the cytostatic effect of cisplatin when the compounds were incubated with cells one hour after cisplatin exposure. Further, it was found that amifostine given 30 minutes after cisplatin did not protect mice at all from nephrotoxicity. Treskes et al. concluded that the selective protection of multiple non-tumor tissue by WR-1065 from cisplatin-induced toxicity is explained by a strong prevention, not reversal, of cisplatin-induced cellular damage. Treskes et al. further observed that these findings were in agreement with the hypothesis that the prevention of damage is the main mechanism of protection and that reversal of platinum-induced damage is not an important mechanism of protection.

Nephrotoxicity, produced by drugs such as cisplatin, has important consequences for the patient, with potential permanent loss of 50% or more of normal renal function (Kemp, et al. *J. Clin. Oncology,* 14:2101–2112, July, 1996). This can produce serious disability, requiring the need for dialysis in severe cases, and early mortality. It also has important consequences for the ability of the patient to be safely treated with other forms of life-sustaining chemotherapy and other medications such as antibiotics that are themselves renally toxic or require adequate renal function for elimination from the body.

Neurotoxicity may significantly decrease a patient's quality of life because of loss or distortion of sensation in the fingers, toes, hands and feet, as well as loss of fine muscle movements, resulting in the inability to perform routine functions such as buttoning of clothes. In more severe cases, patients suffer loss of sufficient motor function so that they require walkers or wheelchairs.

2.2. Cisplatin- and Paclitaxel-Induced Toxicities

Cisplatin continues to be an agent of choice for the treatment of advanced ovarian cancer, testicular cancer, bladder cancer and head, neck and lung cancers. McGuire et al., 1996, "Cyclbphosphamide and cisplatin compared with Paclitaxel and cisplatin in patients with stage III and stage IV ovarian cancer," *N. Engl. J. Med.* 334:1–6. However, the cytotoxic effects of cisplatin on normal tissue, including the kidneys, can result in long-term debilitating effects which may limit the ability to deliver therapeutic doses against the cancer. Despite aggressive hydration and administration of mannitol, cisplatin-induced nephrotoxicity remains a significant cause of morbidity and mortality. Finley et al., 1985, "Cisplatin nephrotoxicity: A Summary of Preventative Interventions," *Drug Intell. Clin. Pharm.* 19:362–367; Kemp et al., 1996, "Amifostine Pretreatment of Protection Against Cyclophosamide-induced and cisplatin-induced toxicities: results of a randomized control trial in patients with advanced ovarian cancer," *J. Clin. Oncol.* 14:2101–2112; Stewart et al., "Association of Cisplatin Nephrotoxicity with patient Characteristics and Cisplatin Administration Methods," *Cancer Chemother. Pharmacol.* 40:293–308.

Even when protective agents are administered prior to or during cisplatin treatment, toxicities may still be observed. The cumulative cisplatin nephro-toxicity that occurs can be treatment-limiting, precluding further administration of -2cisplatin and the ability to administer effective doses of renally-excreted second-line chemotherapy Kemp et al., 1996, *J. Clin. Oncol.* 14:2101–2112. In addition, drug therapy for other conditions can be affected, either because the agents are renally excreted, or because of their intrinsic potential to worsen renal function. Nephrotoxicity is also associated with other platinum coordination complexes such as carboplatin which are also used to treat cancers.

The nephrotoxicity associated with cisplatin is cumulative, i.e., incremental damage occurs with repeated courses of therapy. Daugaard et al., 1989, "Cisplatin nephrotoxicity," *Cancer Chemother. Pharmacol.* 21:1; du Bois, et al., 1994, "Cisplatin and carboplatin induced acute, cumulative and chronic nephrotoxicity," *Proc. Annu. Meet. Am. Assoc. Cancer Res.* 35: A1475. Loss of renal function occurring secondary to cisplatin is typically permanent. Macleod et al., 1988, "The effect of cisplatin on renal function in patients with testicular tumors," *Clin. Radiol.* 39: 190–192; Aass et al., 1990, "Renal function related to different treatment modalities for malignant germ cell tumors," *Br. J. Cancer* 62:842–846; Meijer, et al., 1983, "Influence of combination chemotherapy with cisdiammine chloroplatinum on renal function: Long term effects," *Oncology* 40:170–173. Risk factors for development of this toxic effect include age, a history of renal irradiation, dehydration, and alcoholism. Anand et al., 1993, "Newer insights into cisplatin nephrotoxicity," *Ann. Pharmacother.* 27:1519–1525.

Nephrotoxicity associated with administration of cisplatin and other platinum coordination complexes is generally observed during the second week after a dose and is manifested by elevations in BUN and/or serum creatinine and/or a decrease in creatinine clearance or serum magnesium. Renal toxicity becomes more prolonged and severe with repeated courses of the drug. Nephrotoxicity may be accentuated in patients with pre-existing risk factors such as diabetes or hypertension as well as individuals who are receiving other nephrotoxins such as aminoglycoside antibiotics or antifungals such as amphoterecin. Options available to reduce cumulative cisplatin renal toxicity are limited, and generally involve reducing its dosage or frequency of administration, both of which risk a potential reduction in antitumor effectiveness. Kemp et al., 1996, *J. Clin. Oncol.* 14:2101–2112. Pretreatment or simultaneous administration of amifostine is also an option, but these treatments are not always effective.

In addition to nephrotoxicity, many other toxicities are associated with the administration of platinum coordination compounds. For example, ototoxicity has been observed in up to 31% of patients treated with a single dose of cisplatin (50 mg/m$^2$) and is manifested by tinnitus and/or hearing loss in the high frequency range (4000–8000 Hz). Decreased ability to hear normal conversational tones may occur occasionally. Deafness after the initial dose of cisplatin has been reported rarely. Hearing loss can be unilateral or bilateral and tends to become more frequent and severe with repeated doses. In addition, myelosuppression occurs in 25–30% of patients treated with cisplatin. The nadirs in circulating platelets and leukocytes occur between days 18 to 23 with most patients recovering by day 39. Leukopenia and thrombocytopenia are observed at higher doses (>50 mg/m$^2$).

Neurotoxicity, usually characterized by peripheral neuropathies, is also associated with administration of platinum coordination complexes. The neuropathies, in the form of loss or distortion of sensation, or loss of fine motor function, usually occur after prolonged therapy (4–7 months); however, neurologic symptoms have been reported to occur after a single dose. Although symptoms and signs of cisplatin-induced neuropathy usually develop during treatment, symptoms of neuropathy may begin 3 to 8 weeks after the last dose of the platinum coordination complex.

Generally, in the event of cisplatin-induced neuropathic symptoms, cisplatin is discontinued until the symptoms subside or disappear. The neuropathy, however, may progress even after treatment is stopped. Some preliminary evidence suggests that neuropathy may be irreversible in some patients. Lhermitte's sign, dorsal column myelopathy, autonomic neuropathy, loss of taste and seizures have also been reported. Muscle cramps, defined as localized, painful, involuntary skeletal muscle contractions of sudden onset and short duration, or loss of sufficient motor function so that a patient requires a walker or wheel chair for movement, have been reported and are usually associated in patients receiving a relatively high cumulative dose of cisplatin and exhibiting advanced symptomatic stages of peripheral neuropathy. Amifostine has demonstrated the ability to reduce the incidence of neuropathies when administered prior to cisplatin. In a prospective evaluation of patients treated with cisplatin regimens±amifostine at the Hospital of the University of Pennsylvania Cancer Center, patients pretreated with amifostine had a significantly lower incidence of cisplatin neuropathies and the onset of neuropathies occurred at a significantly higher cumulative dose of cisplatin [Mollman J E, Glover D J, Hogan W M, Furman RE: Cisplatin neuropathy: Risk factors, prognosis and protection by WR-2721. Cancer 61:2192–2195, 1988]. The ability of amifostine pretreatment to significantly reduce the occurrence and severity of cisplatin neuropathy was confirmed in a randomized controlled trial of cisplatin and cyclophosphamide±amifostine in women with advanced ovarian cancer [Kemp G, Rose P, Lurain J et al.: Amifostine pretreatment for protection against cyclophosphamide and cisplatin induced toxicities: Results of a randomized control trial in patients with advanced ovarian cancer. *J. Clin. Oncol.* 14:2101–2112, 1996].

Paclitaxel is indicated, after failure of first-line or subsequent chemotherapy, for the treatment of metastatic carcinoma of the ovary. Paclitaxel is also indicated for the treatment of breast cancer after failure of combination therapy for metastatic disease or relapse within six months of adjuvant therapy. Paclitaxel is known to have the following adverse effects: neutropenia, leukopenia, peripheral neuropathy, and arthralgia/myalgias and other neurological manifestations. The results of a clinical trial of amifostine and escalating doses of paclitaxel, indicated that pretreatment with amifostine allowed both higher single doses and cumulative doses of paclitaxel to be administered without the occurrence of dose limiting neuropathies and arthralgias/myalgias [DiPaolo R et al.: Amifostine and dose intense paclitaxel in patients with advanced malignancies. *Cancer Therapeutics, Proc. Am. Soc. Clin. Oncology* Vol. 16 (Abstract 826) 235a (1997)]. These may be accentuated when the drug is combined with other neurotoxic agents such as cisplatin. Many patients receiving paclitaxel also experience hypotension, asymptomatic bradycardia, and occasional episodes of silent ventricular tachycardia.

Hence, there is a need for a chemical agent for treating symptoms of neurotoxicity and nephrotoxicity which result from the administration of certain therapeutic agents, particularly, chemotherapeutics, radiation therapy, or disease states such as diabetes.

3. SUMMARY OF THE INVENTION

The present invention relates, in part, to methods for treating toxicities associated with the administration to a mammal of one or more therapeutic agents, which comprise administering a therapeutically effective amount of one or more aminothiol compounds, or pharmaceutically acceptable salts thereof, to the mammal after the occurrence of one more of the toxicities. It has been unexpectedly discovered that amifostine and its salts, metabolites, analogues and derivatives can be used to treat or reverse neuro- and nephro-disorders that occur in humans as a result of a variety of insults, including, but not limited to, treatment with therapeutic agents, cancer chemotherapy and/or radiation therapy. The present invention also relates to methods for treatment of neuro- and nephro-disorders resulting from a variety of metabolic disorders, including, but not limited to diabetes. The invention further encompasses methods for the treatment of neuro- and nephro-disorders induced by an unknown etiology.

Thus, in one embodiment, the present invention relates to a method for treating toxicities associated with administration of a chemotherapeutic agent wherein amifostine, or salts, metabolites, functional derivatives, functional analogues, esters and pro-drugs thereof, are administered subsequent to administration of the chemotherapeutic agent, or alternatively, at the first indication of toxicity caused by the chemotherapeutic agent(s). The present invention further relates to methods for treating toxicities associated with the administration of therapeutic agents by administering amifostine, or salts, metabolites, functional derivatives, functional analogues, esters and pro-drugs thereof after clinical appearance of toxicities following therapeutic treatment. In another embodiment, the invention relates to methods of treating toxicities associated with the exposure of a mammal to radiation therapy, which comprise administering to the mammal a therapeutically effective amount of one or more aminothiol compounds, or a pharmaceutically acceptable salt thereof, after the occurrence of the toxicity.

In particular, the present invention provides a method for treating neurotoxicity and nephrotoxicity associated with the administration of a chemotherapeutic agent which comprises administering a therapeutically effective amount of amifostine or a salt, metabolite, ester, functional derivative, functional analogue and pro-drugs thereof, subsequent to the administration of the chemotherapeutic agent. In a preferred embodiment, a compound of the invention is administered one or more days after the administration of the chemotherapeutic agent, preferably, after the disorder has appeared and been established.

Toxicities which are treatable according to the methods of the invention include, but are not limited to, those associated with administration of chemotherapeutic agents including but not limited to cisplatin, carboplatin, paclitaxel, docetaxel, vincristine, navelbine, gemcitabine, topotecan, irinotecan, doxorubicin, and other drugs disclosed herein. Other disorders, toxicities and toxicity-causing agents are described herein.

In still another embodiment, the present invention relates to methods for treating neuro- or nephro-disorders which comprise administering a therapeutically effective amount of one or more aminothiol compounds, or pharmaceutically acceptable salts thereof, to a patient in need of such treatment, after the occurrence of the neuro- and nephro-disorders. The disorder may be chemically induced, drug induced, induced by aging, induced by exposure to radiation or induced by a variety of metabolic disorders, including, but not limited to diabetes. In addition, the disorder may be a neurotoxicity or nephrotoxicity associated with the administration of radiation therapy of one or more therapeutic agents. The methods of the present invention are also suitable for the treatment of disorders induced by an unknown etiology. Neuro-disorders which are treatable according to the methods of the invention include, but are not limited to, peripheral neuropathy, autonomic neuropathy, central neuropathy, muscle weakness, arthralgia or myalgia. The present invention also relates to methods of treating the clinical symptoms and disorders associated with Type I or Type II diabetes in a human in which a therapeutically effective amount of one or more aminothiol compounds or a salt, hydrate or metabolite thereof, is administered to a diabetic human.

4. BRIEF DESCRIPTION OF THE FIGURES

FIG. 1 is a graph showing serum creatinine levels (mg/dL) of a 61-year-old patient suffering from renal failure induced by cisplatin given in combination with paclitaxel. The graph shows a starting serum creatinine level of about 1.0 mg/dL before administration of cisplatin, a maximum level of about 5.5 mg/dL after administration of cisplatin, and a drop in serum creatinine level to about 2.8 mg/dL following treatment with amifostine.

5. DETAILED DESCRIPTION OF THE INVENTION

There are presently a number of chemotherapeutic agents that can be used against various cancers, including solid tumors and leukemias. Unfortunately, these chemotherapeutics frequently cause adverse or undesirable side effects which limit the clinician's ability to use the drug effectively. Most significantly, chemotherapeutics can cause tissue damage, organ damage and the like, which is not only painful to the patient but can also be irreversible or lethal depending upon the patient's tolerance and condition.

The inventors have quite surprisingly and unexpectedly found that the administration of amifostine, and related aminothiol compounds disclosed herein, can be used to reverse or treat the toxicities associated with the administration of various chemotherapeutics, particularly platinum coordination complexes such as cisplatin and paclitaxel. More specifically, upon clinical evidence of neuro- or nephrotoxicity commonly associated with the administration of cisplatin or paclitaxel, amifostine or related compounds can be used to rescue the patient thereby improving the overall treatment/therapy.

Based in part on this discovery, the present invention encompasses a method of treating neuro- or nephro-disorders in a human which comprises administering a therapeutically effective amount of amifostine, or a pharmaceutically acceptable salt, ester, analogue, metabolite, derivative or pro-drug thereof. The neuro- and nephro-toxicities which are treatable according to the methods of the present invention can arise from a variety of insults including, but not limited to cancer chemotherapy, radiation therapy, AIDS, chemotherapy, anti-fungal therapy, anti-bacterial therapy, and I.V. Contrast Agents. These aminothiol compounds can also be used to treat neuro- and nephro-disorders that are induced by aging and metabolic disorders, including, but not limited to diabetes. The methods of the present invention are also suitable for the treatment of neuro- and nephro-disorders induced by an unknown etiology. The methods of the invention are effective for the treatment of patients with and without cancer, as well as cancer patients undergoing or who have undergone chemotherapy. It should be recognized that the present invention also encompasses a method of treating various cancers by the combined use of a chemotherapeutic agent and one or more of the aminothiol rescue agents, such as amifostine, disclosed herein. Indeed, the use of these rescue agents allows the continued use of the chemotherapeutic agent which would have otherwise been discontinued or postponed due to toxicity.

In another embodiment, the present invention provides a method for treating toxicities associated with administration of a therapeutic agent wherein amifostine, or a related compound is administered subsequent to administration of the therapeutic agent. The administration of amifostine, and the compounds disclosed herein, after the occurrence of toxicities associated with administration of the therapeutic agent ameliorates and reverses the signs and symptoms of these toxicities. Thus, the present invention encompasses methods for treating toxicities associated with chemotherapy by administering amifostine, or salts, metabolites, functional derivatives functional analogues, esters and pro-drugs thereof after therapeutic treatment.

The present invention further provides a method for treating toxicities associated with the administration of a chemotherapeutic agent which comprises administering a therapeutically effective amount of amifostine or a metabolite, functional derivative or analogue thereof, or pharmaceutically acceptable salts thereof after the occurrence of one or more of said toxicities.

In particular, the present invention provides a method for treating neurotoxicity and nephrotoxicity associated with the administration of cisplatin or paclitaxel agent which comprises administering a therapeutically effective amount of amifostine or a salt, metabolite, ester, functional derivative, functional analogue and pro-drugs thereof, subsequent to the administration of the chemotherapeutic agent. In a preferred embodiment, the compound is administered after the disorder has appeared and been established, typically one or more days after administration of the chemotherapeutic agent.

The invention also encompasses the use of the aminothiols for the specific treatment of peripheral neuropathy, central neuropathy, autonomic neuropathy, muscle weakness, and myalgaia.

5.1. Aminothiols And Related Compounds that are Useful Within the Invention

As mentioned above, the compounds that can be used within the present invention include amifostine (WR-2721), as well as salts, hydrates, active metabolites, pro-drugs, and functional derivatives or analogues. More specifically, the invention includes all pro-drugs and metabolites of amifostine and pro-drugs of the active metabolites. Thus, compounds known to the skilled artisan to be suitable for administration to humans and known to be metabolites or otherwise converted into active thiols including metabolites such as WR-1065 and WR-33278 (disulfide) and the orally bioavailable WR-151327 and its active thiols, including metabolites such as WR-151326 and its corresponding disulfide, are encompassed within the present invention.

Similarly, described herein are aminothiols that exhibit activity similar to that of amifostine or its metabolites. Preferably, these compounds are structurally related to amifostine. Alternatively, these compounds are pro-drugs that are metabolized in vivo to a biologically active agent. These compounds are also encompassed by the present invention. Specific examples are illustrated herein.

Aminothiol compounds which can be used in the present invention are represented by the following formula (I):

$R_1NH(CH_2)NH(CH_2)_mSR_2$ (I)

$R_1$ is hydrogen, $C_5$–$C_8$ aryl, $C_2C_7$ acyl or $R_1NH(CH_2)_nNH(CH_2)_mS$—; n and m are each an integer from 1 to 10; and preferably an integer from 2 to 6.

The methods of the present invention also encompasses the use of pharmaceutically acceptable salts and hydrates of the compounds of formula (I) above.

Preferred compounds useful in the methods of the invention are the S-ω(ω-amino-alkylamino)alkyl dihydrogen phosphorothioate analogues represented by the formula:

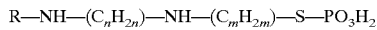
R—NH—$(C_nH_{2n})$—NH—$(C_mH_{2m})$—S—$PO_3H_2$ wherein R is hydrogen or an alkyl group containing 1 to 7 carbon atoms and m and n independently have a value of from 1 to 10, preferably 2 to 6.

The chemical structure of amifostine (WR-2721) can be depicted as follows:

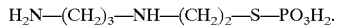
$H_2N$—$(CH_2)_3$—NH—$(CH_2)_2$—S—$PO_3H_2$.

One preferred metabolite of amifostine is a dephosphorylated free thiol form known as WR-1065 (chemical nomenclature: S-2-(3-aminopropylamino) ethanethiol), which can be depicted as follows:

$H_2N$—$(CH_2)_3$—$NH(CH_2)_2$—SH.

Another preferred metabolite of amifostine is its disulfide, known as WR-33278 (chemical nomenclature: [2-[(aminopropyl)amino]ethanthiol]-N,N'-dithioidi-2,1-ethanediyl)bis-1,3-propanediamine), which can be depicted as follows:

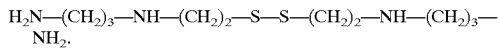
$H_2N$—$(CH_2)_3$—NH—$(CH_2)_2$—S—S—$(CH_2)_2$—NH—$(CH_2)_3$—$NH_2$.

A preferred analogue of amifostine is the compound designated as WR-15327 (chemical nomenclature: 1-propanethiol-3-[[3-(methylamino)propyl]amino]-dihydrogen phosphothiorate), which can be depicted as follows:

$CH_3NH(CH_2)_3NH(CH_2)_3SPO_3H_2$.

Another preferred analogue of amifostine is the compound designated WR-151326, a dephosphorylated free thiol form of WR-151327 having the chemical structure: $CH_3NH(CH_2)_3NH(CH_2)_3SH$.

Other specific compounds suitable for use in the present invention include, but are not limited to:

S-1-(aminoethyl)phosphorothioic acid (WR-638);
S-[2-(3-methylaminopropyl)aminoethyl] phosphorothioate acid (WR-3689);
S-2-(4-aminobutylamino)ethyl phosphorothioic acid (WR-2822);
3-[(2-mercaptoethyl)amino]propionamide p-toluenesulfonate (WR-2529);
S-1-(2-hydroxy-3-amino)propyl phosphorothioic acid (WR-77913);
2-[3-(methylamino)propylamino]ethanethiol (WR-255591);
S-2-(5-aminopentylamino)ethyl phosphorothioic acid (WR-2823);
1-[3-(3-aminopropyl)thiazolidin-2-Y1]-D-gluco-1,2,3,4,5 pentane-pentol dihydrochloride (WR-255709).

Additional aminothiols suitable for use in the present invention include, but are not limited to, S-2-(3-ethylaminopropylamino)ethyl dihydrogen phosphorothioate, S-2-(3-aminopropylamino)-2-methylpropyl dihydrogen phosphorothioate, S-2-(2-aminoethylamino)-2-ethyl dihydrogen phosphorothioate, S-2-(4-aminobutylamino)-2-ethyl dihydrogen phosphorothioate, S-2-(5-aminopentylamino)-2-ethyl dihydrogen phosphorothioate, S-2-(6-aminohexylamino)-2-ethyl dihydrogen phosphorothioate, S-2-(2-methylaminoethylamino)-2-ethyl dihydrogen phosphorothioate, S-2-(3-methylaminopropylamino)-2-ethyl dihydrogen phosphorothioate, and S-3-(3-methylaminopropylamino)-3-propyl dihydrogen phosphorothioate (WR-151327) and pharmaceutically acceptable salts thereof. Preferably, the aminothiol is amifostine, WR-1065, WR-33278, WR-151327 or WR-151326; most preferably it is amifostine.

Amifostine, and many of its salts, analogues and derivatives thereof suitable for use in the methods of the invention are commercially available, or can easily be prepared using standard techniques. The aminothiol compounds useful in the methods of the invention may be prepared by methods known in the art (see, e.g., Cortese, 1943, *Organic Synthesis* pp. 91–93, Coll. Vol. II, Blatt, Ed., John Wiley & Sons, Inc., New York, N.Y.; Akerfeldt, 1960, *Acta Chem. Scand.* 14:1980; Piper et al., 1966, *Chem. Ind.* (London):2010). Certain aminothiol compounds, as well as methods of synthesizing such compounds, are described in detail in U.S. Pat. No. 3,892,824 to Piper et al., U.S. Pat. Nos. 5,424,472 and 5,591,731, both to Kennedy et al., and WO 96/25045, each of which is incorporated herein by reference in its entirety.

The aminothiol compounds useful in the methods of the invention may be in the form of free acids, free bases, or pharmaceutically acceptable addition salts thereof. Such salts can be readily prepared by treating an aminothiol compound with an appropriate acid and/or base. Such acids include, by way of example and not limitation, inorganic acids such as hydrohalic acids (hydrochloric, hydrobromic, hydrofluoric, etc.), sulfuric acid, nitric acid, phosphoric acid, etc. and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

The aminothiol compounds useful in the methods of the invention, as well as the pharmaceutically acceptable addition salts thereof, may be in a hydrated, solvated or anhydrous form. Methods of preparing such forms will be apparent to those of skill in the art of organic chemistry.

5.2. Definitions

As used herein the term "aminothiol" means a compound represented by formula (I) set forth in Section 5.1 above, or any other compound disclosed therein.

The term "rescue agent" as used herein is intended to mean a compound capable of ameliorating, treating, reversing, reducing or arresting the signs and symptoms and pathology associated with the administration of chemotherapeutic agents radiation and pathology of associated diseases.

As used herein the term "disorder" means an illness, a sickness or a disease manifested by an interruption, cessation, derangement or abnormality of body functions, systems or organs.

As used herein, the term "toxicity" means a disorder characterized by a recognized etiologic agent or agents, an identifiable group of signs and symptoms, including adverse effects, unwanted effects, undesired effects, or abnormal signs or symptoms or consistent anatomical alterations.

The preferred subjects of the present invention are mammals, including humans. The subjects include cancer patients that are undergoing or have undergone chemotherapy, radiation treatment or both; AIDS patients and diabetics.

The term "treating" as used herein is intended to mean the administering to a subject the rescue agent of the present invention, preferably amifostine or a functional analogue or derivative thereof, for purposes which may include amelioration of symptoms of, or reversal of toxicities associated with chemotherapy.

As used herein the term "reversing" means that the progress of the disease, disorder or toxicity is inhibited and its symptoms are reversed or improved.

5.3. Toxicities/Disorders to be Treated

The methods of the present invention comprise administration of a pharmaceutical composition which contains an effective amount of an aminothiol of the invention in an acceptable carrier to a subject during or preferably after the subject has received therapy. The aminothiol is preferably amifostine, alone or in combination with one or more other drugs useful in the treatment of toxicities associated with therapy. Also included within the scope of the invention is the administration of compositions comprising a mixture of two or more of the aminothiol compounds of the present invention described above.

The methods of the present invention are suitable for treating toxicities associated with a wide variety of therapeutic agents. In addition, the methods of the invention are suitable for treatment of a variety of neuro- and nephro-disorders resulting from a variety of insults.

5.3.1 Chemically- and Radiation-Induced Toxicities

In one embodiment, the methods of the invention are used to treat toxicities associated with administration of chemotherapeutic agents which include, but are not limited to, cisplatin, carboplatin, paclitaxel, vinblastine, vincristine and methotrexate. In another embodiment, the methods of the invention are used to treat toxicities associated with radiation therapy (x-ray, nuclear and particularly gamma radiation).

The methods of the invention may be used to treat toxicities associated with the administration of the following chemotherapeutic agents: taxanes such as paclitaxel and docetaxel; alkylating agents, which include: nitrogen mustards such as mechlorethamine, cyclophosphamide, ifosamide, melphalan (phenalphenine mustard) and chlorambucil; ethylenimines and methylmelamines such as altretamine, diaziquone (AZQ) and thiotepa; alkyl sulfonates such as busulfan; nitrosoureas such as carmustine (BCNU), lomustine (CCNU), semustine (methyl-CCNU) and streptozocin (streptozotocin); and triazenes such as dacarbazine (DTIC; dimethyltriazenoimidazolecarboxamide); antimetabolites, which include folic acid analogs such as methotrexate, trimetrexate and other dihydrofolates; pyrimidine analogs such as fluorouracil (5-fluorouracil; 5-FU), floxuridine (fluorodeoxyuridine; FUdR) and cytarabine (cytosine arabinoside); purine analogs and related inhibitors such as mercaptopurine (6-mercaptopurine; 6-MP), thioguanine (6-thioguanine; TG) and pentostatin (2'-deoxycoformycin); natural products, which include vinca alkaloids such as vinblastine, vincristine, navelbine and vincristine; epipodophylotoxins such as etoposide and teniposide; antibiotics such as dactinomycin (actinomycin D), daunorubincin (daunomycin; rubidomycin); doxorubicin, bleomycin, plicamycin (mithramycin) and mitomycin (mitomycin C); enzymes such as L-asparaginase; and biological response modifiers such as interferon-alfa and other interferons; platinum coordination complexes such as cisplatin (cis-DDP) and carboplatin; anthracenediones such as mitoxantrone; substituted ureas such as hydroxyurea; methylhydrazide derivatives such as procarbazine (N-methylhydrazine, MIH), and adrenocortical suppressants such as mitotane (o,p'-DDD) and aminoglutethimide; hormones and antagonists which include adrenocorticosteroids such as prednisone; progestins such as hydroxyprogesterone caproate, medroxy progesterone acetate and megestrol acetate; estrogens such as diethylstilbestrol and ethinyl estradiol; antiestrogens such as tamoxifen; androgens such as testosterone propionate and fluoxymetsterone; antiandrogens such as flutamide; and gonadotropin-releasing hormone analogs such as leuprolide; camptothecins such as irinotecan, topotecan; gemciatdins such as gemcitabine; estramustine phosphate, VM-26 (vumon) and all-trans retinoic acid (ATRA). These agents are normally used in the treatment of head and neck, ovarian, breast, colon, lung, prostate, testicular and cervical cancers, as well as certain lymphomas, leukemias, and cancers of the CNS.

The toxicities associated with the administration of these agents or radiation therapy include, but are not limited to nephrotoxicity, neurotoxicity, ototoxicity, myelosuppression, cardiotoxicity, alopecia, infertility and local inflammation from extravasation into the skin, xerostomia and mucositis.

The methods of the present invention are also suitable for treating comparable toxicities associated with anti-virals such as ddI (didanosine), ddC (zalcitabine), d4T (stavadine), 3TC (lamivudine), AZT (zidovudine, 3'azido-3'-deoxythymidine) and the like, anti-bacterials such as aminoglycosides, and anti-fungals, such as amphotericin B.

5.3.2 Nephro-disorders to be Treated

The following nephro-disorders, which are also referred to herein as renal diseases, may be treated according to the methods of the present invention: Various types of glornerulonephritis, including diffuse forms of glornerulonephritis such as acute poststreptococcal, acute nonstreptococcal, rapidly progressive, chronic progressive, and end-stage chronic; focal forms of glomerulonephritis, such as those with systematic bacterial infection, of probable immunologic origin, i.e., IgA focal glomerulonephritis, and hereditary forms; nephrotic syndromes such as minimal change disease, lipoid nephrosis, or nil disease, focal segmental glomerular sclerosis, congenital nephrotic syndrome, membranoproliferative glomerulonephritis, idiopathic membranous nephropathy (membranous glomerulonephritis), systemic lupus erythematosus, systemic infection or hypersensitivity reactions, circulatory disturbances and renal vein thrombosis, amyloidosis, and toxemia of pregnancy; renal diseases of vascular origin such as hypertensive vascular disease, benign nephrosclerosis, malignant nephrosclerosis, diabetic nephropathy, renal infarction, polyarteritis nodosa and Wegener's granulomatosis; thrombotic renal diseases such as disseminated intravascular coagulation, bilateral renal cortical necrosis, hemolytic uremic syndrome, and thrombotic thrombocytopenic purpura; scleroderma; radiation nephritis; tubular diseases such as acute tubular necrosis, including toxic nephropathy and ischemic tubular necrosis, osmotic nephrosis, hypokalemic nephropathy, chronic interstitial and tubular diseases such as interstitial nephritis, pyelonephritis, tuberculous pyelonephritis, urinary tract obstructive disease, renal papillary necrosis, analgesic abuse nephropathy, multiple myeloma nephropathy, gout nephropathy, hypercalcemic nephropathy and renal calcinosis, and renal lithiasis; congenital malformations and anomalies such as agenesis and hypoplasia, fusion, ectopia, and reduplication, dysplasia and polycystic dysplasia, congenital obstructive microcystic disease, simple cysts, infantile polycystic disease, adult polycystic disease, and medullary cystic disease; renal neoplasms such as benign tumors, which include adrenocortical nodules, hamartomas, mesenchymal tumors, and cortical tubular adenomas; and malignant tumors, such as adenocarcinoma, Wilms'tumor, leukemic infiltration, and transitional cell carcinoma.

5.3.3 Metabolic Disorders to be Treated

The present invention provides methods for the treatment of a wide variety of metabolic disorders. One such metabolic disorder is diabetes. The methods of the present invention are also suitable for, the treatment of disorders relating to basal metabolism, i.e., heat production of an individual at the lowest level of cell chemistry in the waking state, or the minimal amount of cell activity associated with the continuous organic functions of respiration, circulation and secretion; carbohydrate metabolism, i.e., the changes that carbohydrates undergo in the tissues, including oxidation, breakdown, and synthesis; electrolyte metabolism, i.e., the changes which the various essential minerals, sodium, potassium, calcium magnesium, etc. undergo in the fluids and tissues of the body; fat metabolism, i.e., the chemical changes, oxidation, decomposition, and synthesis, that fats undergo in the tissues; protein metabolism, i.e., the chemical changes, decompositions, and synthesis that protein undergoes in the tissues; and respiratory metabolism, i.e., the exchange of respiratory gases in the lungs and the oxidation of foodstuffs in the tissues with the production of carbon dioxide and water.

5.3.4 Disorders Associated with Diabetes

Diabetes patients often suffer from numerous debilitating disorders. One such disorder, peripheral neuropathy, is particularly likely to occur in the older diabetic patient, with approximately 30% to 50% of the patients showing minor reflex changes and evanescent pains in the extremities. The basic pathologic change in the peripheral nerves is a segmental demyelination. The autonomic nervous system may also be involved in diabetic patients, with resultant development of severe diarrhea and abdominal pain. Greatly elevated levels of sorbitol and fructose have been demonstrated in peripheral nerves of animals with experimentally induced diabetes. The accumulation of sorbitol and fructose is apparently attributable to a partial shunting of the metabolism of glucose through the aldose reductase pathway. It is unknown whether this abnormal metabolism of glucose with the formation of sorbitol is responsible for the decreased nerve conduction and segmental demyelination in diabetic subjects. In experimental diabetes, degenerative changes have been found in autonomic nerve fibers of the intestinal tract of rats and were associated with the development of megacolon in these animals. Control of the diabetes by islet transplantation resulted in either prevent or disappearance of the degenerative lesions in the autonomic nerves.

Kidney disease is common in diabetes and renal failure is one of the major causes of death. The dominant form of diabetic nephropathy is microvascular disease affecting the renal glomerulus. Early in diabetes, the kidney increases in size and the associated glomerular hypertrophy leads to an increased glomerular filtration rate with hyperfiltration and microalbuminuria in up to 50% of patients with new onset insulin dependent diabetes mellitus. Later in the disease, diffuse thickening of the glomerular basement membrane is noted along with increased mesangial volume and progressive impairment of renal function which in turn leads to further expansion of the mesangium and eventual glomerular occlusion.

Clinically, in some cases mild proteinuria can remain constant for many years, while in other cases it progresses to reduction in glomerular filtration and renal function with all the classical features of nephrotic syndrome. Once azotemia (increased serum creatinine and BUN) develops, progression to renal failure and uremia is inevitable within a few months to two to three years. Once renal failure develops, the only alternatives are dialysis or transplantation.

The treatment of the above disorders is included within the scope of the present invention.

5.4 Effective Dosages

Pharmaceutical compositions suitable for use with the present invention include compositions wherein the active ingredient is contained in a therapeutically effective amount, i.e., an amount effective to achieve its intended purpose. Of course, the actual amount of active ingredient will depend on, among other things, the particular disorder being treated. Determination of an effective amount is well within the capabilities of those skilled in the art.

For any compound described herein the therapeutically effective amount can be initially estimated from cell culture assays. For example, a dose can be formulated in animal models to achieve a circulating concentration range of compound, and/or an active metabolite thereof, that includes an effective concentration as determined in cell culture. Such information can be used to more accurately determine useful doses in humans. See, e.g., Washburn et al., 1976, "Prediction of the Effective Radioprotective Dose of WR-2721 in Humans Through an Interspecies Tissue Distribution Study" *Radiat. Res.* 66:100-5.

Therapeutically effective amounts for use in humans can also be estimated from animal models. For example, a dose for humans can be formulated to achieve a circulating concentration found to be effective in animals.

A therapeutically effective dose can also be estimated from current clinical experience and data, including human pharmacokinetic data. While not intending to be bound by any particular theory, it is believed that efficacy is related to a subject's total exposure to an applied dose of administered drug, and/or an active metabolite thereof, as determined by measuring the area under the blood concentration-time curve (AUC). Thus, a dose administered according to the methods of the invention that has an AUC of administered compound (and/or an active metabolite thereof) within about 50% of the AUC of a dose-known to be effective for the indication being treated is expected to be effective. A dose that has an AUC of administered compound (and/or an active metabolite thereof) within about 70%, 8.0% or even 90% or more of the AUC of a known effective dose is preferred. Adjusting the dose to achieve maximal efficacy in humans based on the methods described above, particularly on the blood concentration and duration of administered compound and/or its active metabolites is well within the capabilities of the ordinarily skilled artisan.

Usual patient doses for administration of amifostine and/or its active metabolite WR-1065 usually range from about 50 mg/day to 6000 mg/day, commonly from about 100 mg/day to 4000 mg/day, and typically from about 200 mg/day to 3500 mg/day. Stated in terms of patient body weight, usual dosages range from about 0.6 to 100 mg/kg/day, commonly from about 1.1 to 66 mg/kg/day, and typically from about 2.2 to 58 mg/kg/day. Stated in terms of patient body surface areas, usual dosages range from about 23 to 4000 mg/m$^2$/day, commonly from about 45 to 2666 mg/m$^2$/day, and typically from about 90 to 2333 mg/m$^2$/day.

For other modes of administration, dosage amount and interval can be adjusted individually to provide effective plasma and/or tissue levels of the administered compound, and/or an active metabolite thereof, according to the pharmacokinetic profiles described herein, as previously described.

The actual amount of composition administered will, of course, be dependent on the subject being treated, the subject's weight, the severity of the affliction, the mode of administration and the judgement of the prescribing physician.

Dosages are in the range of between about 10–1000 mg/m$^2$ administered parenterally. Preferred doses for intravenous administration are between about 100–750 mg per m$^2$ of body surface area, more preferably between about 200–750 mg/m$^2$. Preferred doses for oral administration are between about 20–2000 mg per m$^2$ of body surface area, more preferably between about 500–1500 mg/m$^2$ body surface area.

5.5 Formulations and Dosage Administration

The aminothiol compounds described herein, or pharmaceutically acceptable addition salts or hydrates thereof, can be delivered to a patient according to the invention using a wide variety of routes or modes of administration. Suitable routes of administration include but are not limited to, inhalation, or parenteral routes, including intravenous (infusion or bolus injection), intramuscular, intraperitoneal, intrathecal, subcutaneous, intranasal, transmucosal, buccal, sublingual, vaginal, rectal, intestinal, local intradermal or transdermal routes. Alternatively, or concurrently, administration may be by the oral route. Intravenous administration is particularly desirable.

The aminothiol compounds described herein, or pharmaceutically acceptable salts and/or hydrates thereof, or mixtures thereof, may be administered alone, or in combination with other aminothiol compounds of the invention, and/or in combination with one or more therapeutic agents, including cancer chemotherapeutic agents, intended to also treat the toxicity or disorder suffered by the subject being treated. Examples of such additional drugs include but are not limited to vitamins, in particular the B complex.

Medicaments are considered to be provided "in combination" with one another if they are provided to the subject concurrently, sequentially or if the time between the administration of each medicament is such as to permit an overlap of biological activity.

The aminothiol compounds of the present invention may be administered by any means that achieve their intended purpose. Amounts and regimens for the administration of the aminothiol rescue agents can be determined readily by those with ordinary skill in the clinical art of treating neuro- and nephro-disorders, toxicities or cancer.

It is understood that the dosage of the aminothiol compound will be dependent upon the age, sex, health, and weight of the recipient, kind of concurrent treatment, if any, frequency of treatment, and the nature of the effect desired. An effective amount of the active compound of the present invention is any amount which would serve to treat or reverse symptoms of the neuro- or nephro-disorder or the neurotoxicity or nephrotoxicity caused by administration of a chemotherapeutic agent in vivo. The ranges of effective doses provided herein are not intended to limit the invention and represent preferred dose ranges. However, the most preferred dosage will be tailored to the individual subject, as is understood and determinable by one of ordinary skill in the art without undue experimentation.

For any mode of administration, the actual amount of compound delivered, as well as the dosing schedule necessary to achieve the advantageous effects described herein, will also depend, in part, on such factors as the bioavailability of the compound (and/or an active metabolite thereof), the disorder being treated, the desired therapeutic dose, and other factors that will be apparent to.those of skill in the art. The actual amount delivered and dosing schedule can be readily determined by those of skill without undue experimentation by monitoring the blood plasma levels of administered compound and/or an active metabolite thereof, and adjusting the dosage or dosing schedule as necessary to achieve the desired therapeutic effect. Additionally the dosage or dosing schedule can be adjusted as necessary to achieve the desired therapeutic effect by monitoring the signs and symptoms of the disorder.

The active compoundis) may be administered alone or in the form of a pharmaceutical composition, wherein the active compound(s) is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

The present methods also include providing a liquid based dosage form of the active compound suitable for administration to a subject in need thereof. The liquid base may be any liquid capable of transporting the active ingredient into the body without disrupting the activity of the compound or harming the patient. A preferred base is an isotonic solution, which may also contain conventional additives such as sugars. These solutions are useful for both oral and intravenous administration.

For injection, the agents of the invention may be formulated in aqueous solutions, preferably in physiologically compatible buffers such as Hanks's solution, Ringer's solution, or physiological saline. For transmucosal administration, penetrants appropriate to the barrier to be permeated are used in the formulation. Such penetrants are generally known in the art.

Suitable injectable solutions include intravenous subcutaneous and intramuscular injectable solutions. The active compound may also be administered in the form of an infusion solution or as a nasal inhalation or spray.

For intravenous administration, the active compound is preferably administered by drip infusion in an aqueous solution. The active ingredient may be administered in single or divided doses.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

For oral administration, the active ingredient, preferably amifostine or a functional derivative or analogue thereof such as WR-151327, may be a preparation in any dosage form capable of oral administration. Such dosage forms include tablets, hard, or soft gelatin capsules, caplets, dragees, pills, tablets including coated tablets, and solutions including elixirs, suspensions, gels, slurries or syrups, and the like. Pharmaceutical preparations for oral use can be obtained solid excipient, optionally grinding a resulting mixture, and processing the mixture of granules, after adding suitable auxiliaries, if desired, to obtain tablets or dragee cores.

The active compound of the present invention may be administered rectally in the form of suppositories or enemas.

In general, the preparation in which the active compound of the present invention is administered contains from about 0.1 to about 100 percent, preferably from about 25–85 percent, of active compound(s), together with a carrier or excipient. Suitable pharmaceutically acceptable carriers comprise excipients and auxiliaries which facilitate processing of the active compounds into preparations which can be used pharmaceutically. Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the above-mentioned starches as well as carboxymethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, and/or polyethylene glycol.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also .be formulated in rectal compositions such as suppositories or retention enemas, e.g., containing conventional suppository bases such as cocoa butter or other glycerides.

In addition to the formulations described previously, the compounds may also be formulated as a depot preparation.

Such long acting formulations may be administered by implantation, subcutaneous or intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

It will be understood that the aminothiol rescue agents of the invention may be administered in accordance with the methods of the invention at any time during or after administration of the chemotherapeutic agent, preferably after administration. For example, the rescue agent may be administered one hour after, or more preferably, four or more hours after administration of the chemotherapeutic agent. Most preferably, the rescue agent is administered days, or even weeks after chemotherapy. The rescue agent may be administered after toxicities associated with administration of chemotherapy are observed. Preferably, the rescue agent is administered after chemotherapeutically-induced toxicities are observed or demonstrated.

Indications of toxicity in a patient who has received chemotherapy are well known to those of ordinary skill in the art of treating cancer patients. For example, indications or "markers" of neurotoxicity caused by chemotherapy include, but are not limited to clinical signs and symptoms, nerve conduction studies, and vibrometer measurements. Markers of nephrotoxicity caused by chemotherapy include, but are not limited to increased levels of serum creatinine above 1.5 mg/Dl, BUN greater than 20, abnormal electrolytes, for example decrease in serum, magnesium, bicarbonate or elevations in serum potassium. Preferably, the aminothiol compounds of the invention are administered after one or more of such toxicity markers are observed following chemotherapeutic treatment.

It will be understood that the aminothiol compounds of the invention may be administered according to the methods of the invention after any one or more cycles of administration of a chemotherapeutic drug. For example, the rescue agent may be administered after one cycle of administration of a chemotherapeutic agent, but prior to the next cycle of administration of chemotherapeutic agent.

Having now generally described the invention, the same will be more readily understood through reference to the following examples which are provided by way of illustration, and are not intended to be limiting of the present invention, unless specified.

6. WORKING EXAMPLES

6.1. Example 1

Case Study

A 61-year-old patient with new onset cisplatin-induced renal failure that was identified 6 days post-cisplatin therapy was treated with amifostine 400 mg intravenously for 3 days, with partial recovery of her renal function and improvement in her overall clinical status.

The patient was referred by her primary care physician for a gynecologic evaluation for complaints of increasing pain in her lower abdomen with costovertebral angle tenderness over a 10-month period. Ovarian cysts were identified and monitored by ultrasound on several occasions during that time. The patient had a history of recurrent urinary tract infections, and she had a stent placed for approximately two weeks prior to the gynecologic consult. A CAT scan at that time revealed ureteral stenosis and slight hydronephrosis of her right kidney. Other relevant past medical history included congenital absence of her left kidney, double uteri, and a total abdominal hysterectomy and left salpingo-oophorectomy approximately 30 years previously.

The patient underwent an exploratory laparotomy to determine if the etiology of her increasing pain was secondary to the cystic ovary, urinary tract infections, or ureteral stenosis and hydronephrosis. The patient was found to have grade III papillary adenocarcinoma arising from a serious type adenofibroma, with metastasis to the omentum. A right oophorectomy and partial omentectomy were performed, with lysis of adhesions. Repeat surgery was performed approximately one month later for lymph node biopsy for staging of the cancer and to remove additional omentum. Intraperitoneal and intravenous (iv) catheters were placed at this time for future chemotherapy.

The patient was evaluated for chemotherapy and was placed on a treatment regiment consisting of paclitaxel 135 $mg/m^2$ (223 mg) administered iv on day 1, followed by cisplatin 100 $mg/m^2$ (165 mg) intraperitoneally on day 2. However, after receiving days 1 and 2 of chemotherapy, the patient presented to the emergency room on day 3 with nausea, vomiting, and abdominal cramping. She was admitted for hydration and treatment of nausea. For the next 5 days, she continued to complain of nausea and vomiting, despite treatment with intensive antiemetic regimens, including granisetron, dexamethasone, and promethazine. Other treatment at that time included ketorolac for pain, lorazepam for anxiety, and large volumes of iv fluids. By hospital day 5, the patient's serum creatinine had risen to 4.9 mg/Dl and the BUN to 39 mg/Dl. Electrolyte abnormalities at that time were: sodium—128 mMol/L, potassium—1.9 Mmol/L, chloride—94 Mmol/L, and $CO_2$-22 Mmol/L. Also, the serum calcium was 4.5 mMol/L. The patient was transferred to telemetry for observation and normalization of her electrolytes.

A renal consultation determined the patient's acute renal failure to be secondary to cisplatin therapy and complicated by volume depletion. She continued to be rehydrated, and further chemotherapy was withheld. Because of persistent, unresponsive renal failure, amifostine 400 mg per day was administered intravenously on post-cisplatin days 7, 8, and 9 in an effort to reduce the drug-induced nephrotoxicity. The patient tolerated therapy well, with only mild nausea. Her renal function improved over the next 3 days on amifostine, with her creatinine decreasing from a peak concentration of 6.0 mg/dL before amifostine to 4.6 mg/dL on day 3 of amifostine therapy. At that time, her electrolytes had normalized, her abdominal cramping significantly lessened, and she was able to tolerate oral fluids. By hospital day 12, the patient's creatinine had decreased to 2.8 mg/dL. and she was discharged on hospital day 13. The patient's response to amifostine therapy, as demonstrated by improvement in serum creatinine, is shown in FIG. 1.

Two days later the patient was readmitted with dystonia caused by increased promethazine usage for intractable nausea and vomiting. The patient was hydrated and monitored over the next 5 days, and electrolyte abnormalities were corrected. Amifostine 400 mg iv was administered once again on hospital day 2, with ondansetron 24 mg administered as needed for nausea. The patient tolerated the treatment well. Her renal function stabilized during this hospitalization, with creatinine/BUN ranging between 2.8/17 mg/dL and 3.2/13 mg/dL. She was discharged on hospital day 5.

A follow-up clinic visit was scheduled for 3 days post-discharge, at which point the patient chose not to pursue further chemotherapy. Amifostine 400 mg iv was administered 5 days later to assess whether further improvement in her renal function could be achieved. Granisetron 1 mg was given orally as premedication. The patient's creatinine at that time was 2.5 mg/dL. Two weeks later, it was decided to administer a final 2-week course of amifostine 400 mg, with reassessment at the end of therapy. Amifostine was administered every 2 to 3 days for a total of 5 doses over the 2 weeks. Lorazepam 1 mg iv and ondansetron 24 mg iv were administered as premedication. Approximately 6 months later, the patient's serum creatinine was 2.0 mg/dL.

In this Example, the patient received amifostine on days 7 through 9 post-cisplatin therapy, after renal failure had already developed. Amifostine partially reversed the toxic renal effects of cisplatin, with the patient's serum creatinine decreasing over the 3-day course of treatment from 6.0 mg/dL to 4.6 mg/dL, and to 2.8 mg/dL by discharge from the hospital on day 13. Concurrent with her improving renal function, the patient's overall clinical status improved during this time, with normalization of electrolyte imbalances and defervescence of abdominal cramping, nausea, and vomiting.

6.2. Example 2

Case Study

The patient, a 75-year-old white male, who is a survivor of the concentration camps of World War II, was diagnosed with bladder cancer that had metastized to the lungs. He received 3 cycles carboplatinum, vinblastine and methotrexate. While in the concentration camp, the patient suffered damage to his lower legs which caused him constant pain. This pain was made worse by chemotherapy. The tumors were shrinking in his lungs, but he developed severe neurotoxicities of his right arm and refused further treatment. These neurotoxicities seemed to worsen after chemotherapy was stopped. He was given demerol for acute relief and required 2–100 mcg/hr. Duragesic Patches in order to make his pain "bearable." The patient was tried on many other agents and combination of agents including steroids and non-steroidals. Soon the Duragesic patches were no longer making his pain bearable, and he was very depressed, and complaining of sleepiness.

After premedication with antiemetics, the patient was given 500 mg of amifostine in 50 cc 0.9 saline over 10 minutes. Two days later, the patient reported that he had no pain for the first time in months, even the pain in his legs was getting better. He was able to walk without his cane. The patient received subsequent Ethyol infusions and has remained without arm pain. The pain in his legs has improved and he is managing with only one Duragesic Patch.

6.3. Example 3

Case Study

A 72-year-old white female was diagnosed with lung cancer and received 3 cycles of amifostine, paclitaxel, and carboplatin in which the amifostine was administered prior to chemotherapy. By the fourth cycle she was confined to a wheel chair with foot drop and unable to feed herself or brush her teeth because of her neurotoxicities. Chemotherapy had to be stopped even though her tumor was responding to treatment. Several medications were tried along with physical therapy to reduce her problems of neuropathy. When she did not respond to several months of this treatment, Ethyol single agent therapy was initiated.

The patient was premedicated with Zofran (ondanestron) 32 mg, Decadron 20 mg in 50 cc normal saline IVPB over 15 minutes and then given amifostine 970 mg in 50 cc normal saline over 10 minutes. She tolerated this treatment without problems. Two days later, the patient reported improvement in strength in her upper arms and legs. She was able to hold a tooth brush and silverware again. The patient continued to receive weekly infusions of amifostine. By the third treatment, she was walking again with the aid of a walker. However, the day after the fourth treatment with amifostine, the patient experienced erythema and blistering all over her body, which eventually led to total skin peeling. The amifostine treatments were terminated. One month later, the patient's skin was back to normal and her neuropathy remained stable.

6.4 Example 4

Case Study

A 55-year-old male with myelodysplastic bone marrow syndrome (MDS) suffered with neurotoxicities for eight years which developed as a result of CHOP (cyclophosphamide, doxorubicin, vincristine, prednisone) chemotherapy given for Non-Hodgkins Lymphoma. This patient initiated treatment for MDS with Ethyol, 840 mg, Monday, Wednesday and Friday of each week. After receiving five weeks of such amifostine therapy for MDS, the patient stated (unsolicited) that his neurotoxicities were better since receiving amifostine. The patient continues on Ethyol for MDS and is doing well.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A method for treating a nephro-disorders in a human which comprises administering a therapeutically effective amount of one or more aminothiol compounds, or a pharmaceutically acceptable salt thereof, to a human in need of such treatment after the occurrence of said nephro-disorders.

2. The method of claim 1, wherein said nephro-disorder is chemically induced, drug induced, induced by aging, induced by exposure to radiation, induced by diabetes or induced by an unknown etiology.

3. The method of claim 2 wherein said nephro-disorder is induced by diabetes.

4. The method of claim 1, wherein said nephro-disorder is a nephrotoxicity associated with the administration of radiation therapy of one or more therapeutic agent(s).

5. The method of claim 1 wherein said nephro-disorder is characterized by elevations in BUN, serum creatinine, or a decrease in creatinine clearance or sodium magnesium or a combination thereof.

6. The method of claim 4 wherein said therapeutic agent is an antiviral, an antibiotic, an antifungal, a contrast agent or a combination thereof.

7. The method of claim 1 wherein said nephro-disorder is a result of the administration of cisplatin, carboplatin, pactitaxel, docetaxel, vincristine, navelbine, gemcytobin, etoposide, doxorubicin, daunorubicin or a combination thereof.

8. The method of claim 1 wherein said nephro-disorder is a result of the administration of 3'-azido-3'-deoxythymidine (AZT), d4T (stavadine), ddI (didanosine), ddC (zalcitabine), 3TC (lamivudine), gentamicin, tobramicin, kanamicin, amikacin, vancamicin, amphotericin B or a combination thereof.

9. The method of claim 1, wherein said aminothiol compound is administered intravenously, subcutaneously, intramuscularly, intradermally, topically or orally.

10. The method of claim 1 wherein said human is a cancer patient, AIDS patient, diabetic, or hypertensive patient.

11. The method of claim 1 wherein said aminothiol compound is a compound of the formula:

$$R_1NH(CH_2)_nNH(CH_2)_mSR_2$$

or a pharmaceutically acceptable addition salt or hydrate thereof, wherein $R_1$ is hydrogen, $C_5$–$C_7$ aryl, $C_2$–$C_7$ acyl, or $C_1$–$C_7$ alkyl;

$R_2$ is hydrogen, $PO_3H_2$ or $R_3$ wherein $R_3$ is $R_1NH(CH_2)_nNH(CH_2)_mS$—;

n is an integer from 1 to 10; and m is an integer from 1 to 10.

12. The method of claim 11, wherein said compound is selected from the group consisting of WR-1065, WR-151326, WR-151327, WR-638, WR-3689, WR-2822, WR-2529, WR-77913, WR-255591, WR-2823, WR-255709 and salts or hydrates thereof.

13. The method of claim 1, wherein said aminothiol is amifostine.

14. The method of claim 1, wherein said aminothiol is WR-33278.

15. The method of claim 1, wherein said aminothiol is an active metabolite of WR-2721.

16. The method of claim 1, wherein said aminothiol is a prodrug of an active metabolite of WR-2721.

17. The method of claim 1, wherein said aminothiol is administered one or more days after the occurrence of said nephro-disorders.

18. The method of claim 1, wherein two or more aminothiol compounds are administered.

19. The method of claim 1, wherein the amount administered is from about 10 mg/m² to about 2,000 mg/m².

* * * * *

UNITED STATES PATENT AND TRADEMARK OFFICE
CERTIFICATE OF CORRECTION

PATENT NO. : 6,586,476 B1  
APPLICATION NO. : 09/429290  
DATED : July 1, 2003  
INVENTOR(S) : Stogniew et al.

Page 1 of 1

It is certified that error appears in the above-identified patent and that said Letters Patent is hereby corrected as shown below:

Column 9, lines 18-22, please replace

"$R_1NH(CH_2)NH(CH_2)_mSR_2$ $R_1$ is hydrogen, $C_5$-$C_8$ aryl, $C_2C_7$ acyl or $R_1NH(CH_2)_nNH(CH_2)_mS$-;

n and m are each an integer from 1 to 10; and preferably an integer from 2 to 6"

with

--$R_1NH(CH_2)_nNH(CH_2)_mSR_2$ wherein $R_1$ is hydrogen, $C_5$-$C_7$ aryl, $C_2$-$C_7$ acyl, or $C_1$-$C_7$ alkyl;

$R_2$ is hydrogen, $PO_3H_2$ or $R_3$, wherein $R_3$ is $R_1NH(CH_2)_nNH(CH_2)_mS$-; and n and m are each an integer from 1 to 10; and preferably an integer from 2 to 6--

Signed and Sealed this

Twenty-fourth Day of June, 2008

JON W. DUDAS  
*Director of the United States Patent and Trademark Office*